United States Patent [19]

Schubart et al.

[11] 4,331,821
[45] May 25, 1982

[54] PROCESS FOR THE MONOHALOGENATION OF ALKYLBENZENES IN THE α-POSITION AND NEW ALKYLBENZENES MONOHALOGENATED IN THE α-POSITION

[75] Inventors: Rüdiger Schubart, Bergisch-Gladbach; Erich Klauke, Odenthal; Klaus Naumann, Cologne; Rainer Fuchs, Wuppertal, all of Fed. Rep. of Germany

[73] Assignee: Bayer Aktiengesellschaft, Leverkusen, Fed. Rep. of Germany

[21] Appl. No.: 209,765

[22] Filed: Nov. 24, 1980

Related U.S. Application Data

[63] Continuation of Ser. No. 78,991, Sep. 26, 1979, abandoned.

[30] Foreign Application Priority Data

Oct. 11, 1978 [DE] Fed. Rep. of Germany ......, 2844270

[51] Int. Cl.$^3$ .............................................. C07C 17/14
[52] U.S. Cl. .............................. 570/196; 204/158 HA
[58] Field of Search ................. 570/196; 204/158 HA

[56] References Cited

U.S. PATENT DOCUMENTS

| | | | |
|---|---|---|---|
| 1,761,475 | 6/1930 | Gubelmann et al. | 204/158 HA |
| 2,563,820 | 8/1951 | Darragh et al. | 204/158 HA |
| 3,465,051 | 9/1969 | Pecherer | 570/195 |
| 3,489,784 | 1/1970 | Fellig et al. | 570/144 |
| 3,517,056 | 6/1970 | DeGaetano | 570/197 |
| 4,092,369 | 5/1978 | Gelfand | 570/197 |

*Primary Examiner*—Curtis R. Davis

*Attorney, Agent, or Firm*—Sprung, Horn, Kramer & Woods

[57] ABSTRACT

A process for the monohalogenation of alkylbenzenes in the α-position is disclosed wherein an alkylbenzene reactant containing a hydrogen atom in the α-position is contacted with a halogen and the reaction mixture is withdrawn such that the amount of monohalogenated alkylbenzene formed is no greater than 33 mol percent in the reaction mixture. Also disclosed are novel monohalogenated alkylbenzenes of the formula

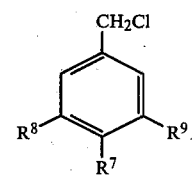

in which
$R^7$ represents trifluoromethoxy, trifluoromethylthio or 2-perfluoropropyl or also, if $R^8$ represents chlorine, represents trifluoromethyl and, furthermore, if
$R^8$ and $R^9$ represent trifluoromethyl, represents hydrogen,
$R^8$ represents hydrogen or also, if $R^7$ represents trifluoromethyl or trifluoromethoxy, represent chlorine and also, if $R^7$ represents hydrogen and $R^9$ represents trifluoromethyl, denotes trifluoromethyl and
$R^9$ represents hydrogen and, if $R^7$ represents hydrogen and $R^8$ represents trifluoromethyl, denotes trifluoromethyl.

11 Claims, 1 Drawing Figure

PROCESS FOR THE MONOHALOGENATION OF ALKYLBENZENES IN THE α-POSITION AND NEW ALKYLBENZENES MONOHALOGENATED IN THE α-POSITION

This is a continuation, of application Ser. No. 078,991, filed Sept. 26, 1979 and now abandoned.

BACKGROUND OF THE INVENTION

Field of the Invention

The invention relates to a process for the monohalogenation of alkylbenzenes in the α-position and to new alkylbenzenes monohalogenated in the α-position.

Discussion of Prior Art

It is known to chlorinate alkylbenzenes, for example toluene, in the side chain with elementary chlorine at elevated temperature and with exposure to UV light. By-products are formed in this reaction, for example benzal chloride, benzotrichloride, products chlorinated in the nucleus and condensed, high-boiling by-products are additionally formed when toluene is chlorinated to benzyl chloride (Houben-Weyl, Methoden der organischen Chemie (Methods of Organic Chemistry), volume V/3, page 736, Georg Thieme Verlag Stuttgart, 1962).

SUMMARY OF THE INVENTION

A process for the monohalogenation of alkylbenzenes in the α-position has been found which is characterised in that an excess of an alkylbenzene which has at least one hydrogen atom in the α-position and which optionally contains water up to saturation concentration, is reacted continuously with a halogen in the temperature range of about 80° C. up to the boiling point of the alkylbenzene employed and in the presence of light containing UV radiation, the halogenation being carried out to an extent such that the concentration of the halogenoalkylbenzene, newly formed by monohalogenation, in the reaction mixture continuously withdrawn from the reaction space is not more than about 33 mol %, relative to the number of mols of all of the substances contained in the reaction mixture.

Examples which can be mentioned of alkylbenzenes which have at least one hydrogen atom in the α-position are those of the formula

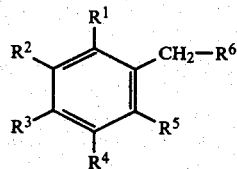

(I)

in which $R^1$ to $R^5$ can be identical or different and represent hydrogen, alkyl, halogenoalkyl, aryl, aralkyl, alkoxy, aryloxy, halogen, isocyanate, nitro, chlorosulphonyl, chlorocarbonyl or cyano and, in addition, two adjacent radicals $R^1$ to $R^5$ together can form an alkylene group, or together with the carbon atoms which carry them can represent a fused aromatic ring, and $R^6$ denotes hydrogen, halogen, alkyl or aryl.

Examples of alkyl which may be mentioned are straight-chain or branched hydrocarbon radicals with 1 to 4 carbon atoms, such as methyl, ethyl, propyl, isopropyl, butyl or isobutyl. The preferred alkyl is the methyl radical.

Examples which may be mentioned of halogenoalkyl are partially or completely halogenated straight-chain or branched hydrocarbon radicals with 1 to 4 carbon atoms, such as chloromethyl, dichloromethyl, trichloromethyl, bromomethyl, dibromomethyl, tribromomethyl, monofluoromethyl, difluoromethyl, trifluoromethyl, monofluorodichloromethyl, difluoromonochloromethyl, partially or completely halogenated ethyl radicals, partially or completely halogenated propyl radicals and partially or completely halogenated butyl radicals. The trichloromethyl radical and the trifluoromethyl radical are preferred halogenoalkyl.

Examples which may be mentioned of aryl are aromatic radicals with 6 to 14 carbon atoms, such as phenyl, naphthyl, anthryl or diphenyl. The preferred aryl is phenyl.

Examples which may be mentioned of aralkyl are hydrocarbon radicals with 1 to 2 carbon atoms in the aliphatic part and 6 to 14 carbon atoms in the aromatic part, such as benzyl, β-phenyl-ethyl, naphthyl-methyl, naphthyl-ethyl, anthryl-methyl, anthryl-ethyl, ortho-, meta- and para-diphenyl-methyl and ortho-, meta- or para-diphenyl-ethyl.

The preferred aralkyl is the benzyl radical.

Examples which may be mentioned of alkoxy are radicals which are derived from a $C_1$–$C_4$ alcohol, such as methoxy, ethoxy, propoxy, isopropoxy, butoxy or isobutoxy. The preferred alkoxy is the methoxy radical.

Examples which may be mentioned of aryloxy are radicals which are derived from a phenolic compound such as phenoxy, diphenyloxy, napthyloxy or anthryloxy i.e. from 6 to 18 carbocyclic carbon atoms. The preferred aryloxy is the phenoxy radical.

The elements fluorine, chlorine, bromine or iodine, preferably fluorine, chlorine or bromine, can be the halogen.

If two adjacent radicals $R^1$ to $R^5$ together form an alkylene group, alkylene groups which can be formed are those with 3 to 4 carbon atoms, which optionally can carry further lower alkyl radicals, for example trimethylene, methyl-substituted trimethylene, tetramethylene or methyl-substituted tetramethylene.

Furthermore, two adjacent groups $R^1$ to $R^5$, together with the carbon atoms which carry them, can represent a fused aromatic ring, so that, including the aromatic ring which carries the substituents $R^1$ to $R^5$, for example the naphthalene system forms.

Examples which may be mentioned of starting compounds of the formula (I) for the process according to the invention are: toluene, ortho-xylene, meta-xylene, para-xylene, mesitylene, durol, 1,2,4-trimethylbenzene, pentamethylbenzene, hexamethylbenzene, ortho-chlorotoluene, meta-chlorotoluene, para-chlorotoluene, ortho-fluorotoluene, meta-fluorotoluene, para-fluorotoluene, ortho-bromotoluene, meta-bromotoluene, para-bromotoluene, ortho-cyanotoluene, meta-cyanotoluene, para-cyanotoluene, dichlorotoluene, trichlorotoluene, difluorotoluene, trifluorotoluene, ortho-phenoxytoluene, meta-phenoxytoluene, para-phenoxytoluene, phenoxy-chlorotoluene, phenoxy-fluorotoluene, ortho'-, meta'- and para'-chloro-phenoxytoluene, ortho'-, meta'- and para'-fluorophenoxytoluene, methylnaphthalene, methylbiphenyl, tetrafluorotoluene, pentafluorotoluene, ortho-, meta- and para-nitrotoluene;

ortho-, meta- and para-chlorosulphonyltoluene, benzyl chloride, and all the isomeric toluenes substituted in the benzene nucleus by chlorine and fluorine, by bromine and fluorine and by iodine and fluorine.

An example of an excess of the starting materials of the formula (I) relative to the halogen is a ratio of 2 to 50 mols and preferably 3 to 20 mols of alkylbenzene of the formula (I) per mol of halogen.

The starting materials of the formula (I) can be employed in the process according to the invention in the form of anhydrous substances. However, it has been found that water-containing substances of the formula (I) can also be employed without impairing the reaction in the process according to the invention. An example of the water content which may be mentioned is a water content of up to saturation concentration.

An example of halogenation of the starting materials of the formula (I) in the process according to the invention is the reaction with chlorine or bromine. The reaction with chlorine is preferred.

In the process according to the invention, the halogen is introduced as a gas into the reaction space. The halogen can be employed without further diluent, but one can also dilute the gaseious halogen with inert gases, for example with nitrogen or with argon. The proportion of the diluent can be up to 90% and preferably 30 to 50% of the halogen/inert gas mixture employed.

The reaction according to the invention is carried out in the presence of light containing UV radiation, for example by irradiating the reaction mixture with a high-pressure or low-pressure mercury lamp.

The process according to the invention is carried out at elevated temperature. An example of such a temperature which may be mentioned is a range from about 80° C. up to the boiling point of the alkylbenzene of the formula (I). The temperature range from 30° C. below the boiling point up to the boiling point of the alkylbenzene is preferred and the range from 10° C. below the boiling point up to the boiling point is particularly preferred.

The process according to the invention can be carried out under normal pressure or excess pressure, preferably under normal pressure.

The halogenation in the process according to the invention is carried out to an extent such that the concentration of the halogenoalkylbenzene, newly formed by the monohalogenation, in the reaction mixture which is withdrawn from the reaction space is not more than about 33 mol %, relative to the number of mols of all of the substances contained in the reaction mixture. A concentration of 0.1 to 33 mol % and preferably 2–25 mol % may be mentioned by way of example.

The process according to the invention is carried out continuously.

The reaction space is appropriately so designed that the liquid alkylbenzene and the gaseous halogen, which is optionally diluted with inert gas, are mixed well. For example, the reaction space can contain inserts, such as a frit, through the pores of which the halogen passes into the alkylbenzene which is flowing by, or a hollow cone with an annular nozzle, which functions in a similar manner. The reaction space can also, for example, be in the form of a Venturi tube.

The reaction mixture can be worked up by customary measures, for example distillation, crystallisation or absorption, preferably by distillation. The end product obtainable from the working up can subsequently be further purified, for example by fractional distillation.

During working up, the alkylbenzene employed in excess can be recovered and re-employed in the process according to the invention.

The process according to the invention is generally carried out by introducing the alkylbenzene, which is in excess relative to the halogen, and the halogen into the reaction space and reacting them there in the temperature range according to the invention, under the action of light containing UV radiation. The reaction temperature, the level of the molar excess of the alkylbenzene, relative to the halogen, and the residence time of the reaction mixture in the reaction space are so chosen, depending on the starting materials, that the halogen is virtually completely converted in the reaction space. The reaction mixture is continuously removed from the reaction space and worked up by distillation.

In the process according to the invention one can prepare compounds of the formula

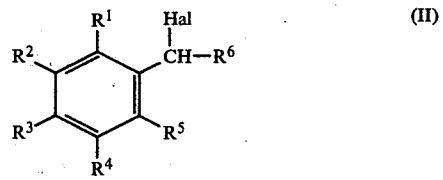

in which

R¹ to R⁶ have the meaning indicated above and

Hal represents chlorine or bromine, for example: benzyl chloride, benzyl bromide, 2-methylbenzyl chloride, 2-methylbenzyl bromide, 3-methylbenzyl chloride, 3-methylbenzyl bromide, 4-methylbenzyl chloride, 4-methylbenzyl bromide, 2-chloromethyl-benzyl chloride, 3-chloromethyl-benzyl chloride, 4-chloromethyl-benzyl chloride, 3,4-dimethylbenzyl chloride, 3-methyl-4-chloromethylbenzyl chloride, 2-chlorobenzyl chloride, 3-chlorobenzyl chloride, 4-chlorobenzyl chloride, 2-chlorobenzyl bromide, 3-chlorobenzyl bromide, 4-chlorobenzyl bromide, 2,4,5-trimethylbenzyl chloride, 2,4,5-trimethylbenzyl bromide, tetramethylbenzyl chloride, tetramethylbenzyl bromide, pentamethylbenzyl chloride, pentamethylbenzyl bromide, α-methylbenzyl chloride, α-methyl-benzyl bromide, dichlorobenzyl chloride, trichlorobenzyl chloride, tetrachlorobenzyl chloride, 2-chlorocarbonyl-benzyl chloride, 3-chlorocarbonyl-benzyl chloride, 4-chlorocarbonyl-benzyl chloride, 2-fluoro-benzyl chloride, 3-fluorobenzyl chloride, 4-fluorobenzyl chloride, 2-fluorobenzyl bromide, 3-fluorobenzyl bromide, 4-fluorobenzyl bromide, 2-cyanobenzyl chloride, 3-cyanobenzyl chloride, 4-cyanobenzyl chloride, fluoro-chloro-benzyl chloride, fluoro-bromo-benzyl chloride, fluoro-bromo-benzyl bromide, isocyanatobenzyl chloride, chloroisocyanatobenzyl chloride, fluoro-isocyanato-benzyl chloride, fluoro-fluorocarbonyl-benzyl chloride, fluoro-cyano-benzyl chloride, fluoro-methyl-benzyl chloride, fluoro-methyl-benzyl bromide, chloro-methyl-benzyl chloride, chloro-cyano-benzyl chloride, 3-phenoxy-benzyl chloride, 4-fluorophenoxy-benzyl chloride, chlorophenoxybenzyl chloride, phenoxy-chloro-benzyl chloride, 2-bromobenzyl chloride, 3-bromobenzyl chloride, 4-bromobenzyl chloride, 2-bromobenzyl bromide, 3-bromobenzyl bromide, 4-bromobenzyl bromide; methoxy-chloro-benzyl chloride, 3-phenoxy-4- fluoro-benzyl chloride, phenyl-benzyl chloride, 2-trifluoromethylbenzyl chloride, 3-trifluoromethylbenzyl chloride, 4-trifluoromethylbenzyl chloride, 3-trifluoromethyl-6-chlorobenzyl chloride, 4-trifluoromethyl-5-chloro-benzyl chloride, 2-chloro-4-trifluoromethyl-benzyl chloride, 2-chloro-3-trifluoromethyl-benzyl chloride, 3-trifluoromethyl-4-chlorobenzyl chloride, 2,6-difluoro-benzyl chloride, 2,4-difluoro-benzyl chloride, 2-chlorocarbonyloxy-benzyl chloride, 4-trifluoromethylthio-benzyl chloride, 4-trifluoromethyloxy-benzyl chloride, 3-chloro-4-trifluoromethyloxy-benzyl chloride, 4-heptafluoroisopropyl-benzyl chloride, 3,5-di(trifluoromethyl)-benzyl chloride, 4-isocyanato-benzyl chloride, 3-chloro-6-isocyanato-benzyl chloride, 4-chloro-6-isocyanato-benzyl chloride, 5-chloro-6-isocyanato-benzyl chloride, 2-chloro-6-isocyanato-benzyl chloride, 2-fluoro-6-isocyanato-benzyl chloride, 3-fluoro-6-isocyanato-benzyl chloride, 4-fluoro-6-isocyanato-benzyl chloride, 2,3-dichloro-6-isocyanato-benzyl chloride, 3,5-dichloro-6-isocyanato-benzyl chloride, 2,3,4-trichloro-6-isocyanato-benzyl chloride, 2,3,4,5-tetrachloro-6-isocyanato-benzyl chloride, 4-trifluoromethyl-6-isocyanato-benzyl chloride, o-nitro-benzyl chloride, m-nitrobenzyl chloride, p-nitrobenzyl chloride, 2-methyl-3-nitrobenzyl chloride, 2-methyl-4-nitrobenzyl chloride, 2-methyl-5-nitrobenzyl chloride, o-chlorosulphonylbenzyl chloride, m-chlorosulphonylbenzyl chloride, p-chlorosulphonylbenzyl chloride and benzal chloride.

The substituted benzyl chlorides of the formula

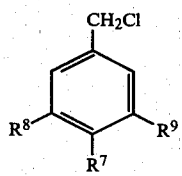

(III)

in which $R^7$ denotes trifluoromethoxy, trifluoromethylthio or 2-perfluoropropyl or also, if $R^8$ represents chlorine, denotes trifluoromethyl and, furthermore, if $R^8$ and $R^9$ represent trifluoromethyl, denotes hydrogen, $R^8$ represents hydrogen or also, if $R^7$ represents trifluoromethyl or trifluoromethoxy, denotes chlorine and also, if $R^7$ represents hydrogen and $R^9$ represents trifluoromethyl, denotes trifluoromethyl, and $R^9$ represents hydrogen and, if $R^7$ represents hydrogen and $R^8$ represents trifluoromethyl, denotes trifluoromethyl, which can be prepared by the process according to the invention are new.

The compounds, including the new compounds, which can be prepared according to the invention by monohalogenation of alkylbenzenes in the α-position can be used as intermediate products for the preparation of plant protection agents, for example, of herbicidal active compounds.

Thus, according to DE-OS (German Published Specification) No. 1,668,243, for example the 3-trifluoromethyl benzylchloride can be reacted with sodium cyanide in the presence of dimethyl formamide at elevated temperature to yield the 3-trifluoromethyl benzylcyanide which is itself a valuable herbicide but which can be further hydrolized partially to yield the 3-trifluoromethylphenyl acetic acid amide by virtue of concentrated hydrochloric acid at 40° C. or hydrolized completely by 10% by weight aqueous NaOH at the boiling temperature of the reaction mixture to yield the 3-trifluoromethylphenyl acetic acid. Both the said substituted acetic acid amide and the said free substituted acetic acid have a broad herbicidal effectiveness. According to GB No. 1,238,522 the 3-trifluoromethyl benzylchloride can be first reacted with sodium or potassium cyanide to yield 3-trifluoromethyl benzyl cyanide which in turn is hydrolized completely to the corresponding substituted acetic acid chloride which in turn can be reacted with dimethylamine to yield 3-trifluoromethylphenyl-N,N-dimethylacetamide which has herbicidal, nematocidal and fungicidal activity. Optionally substituted benzylhalides can be converted by known manners first to the corresponding benzylcyanides and, by hydrogenation, to the corresponding benzylamines which in turn can be reacted for example with N-tert-butyl-2-benzothiazole sulfenamide at 80° to 90° C., according to DE-OS (German Published Specification) No. 1,941,884, to yield 2-benzylaminethio benzothiazol which can serve as a vulcanization accelerator. Furthermore, the optionally substituted benzyl halides, for example 4-chlorobenzyl chloride can be reacted with potassium hydroxide with propane-1,3-diole to yield 3-(4-chloro-benzyloxy)-propane-1-ol which can be further reacted, according to DE-OS (German Published Specification) No. 2,365,762, with 1-amino 2-phenoxy-4-hydroxy-anthraquinone in the presence of potassium carbonate at a temperature of 160° C. to yield the corresponding anthraquinone dyestuff which dyes polyester and polyamide fibres in a brilliant pink colour. Furthermore the optionally substituted benzyl halides can be used in the Sommelet process to yield the corresponding benzaldehydes (Houben-Weyl, Handbuch der Organischen Chemie (Handbook of Organic Chemistry), Vol. VII/1, page 194, Georg Thieme Verlag Stuttgart 1954), which are useful odorous substances or valuable intermediates for various purposes.

Furthermore, the optionally subst. benzylhalides are useful for the preparation of selective benzylicether-herbicides according to German Offenlegungsschrift No. 2724 675.

Thus, benzylchloride or benzylbromide can be reacted at elevated temperature with the alkololate from 3-hydroxytetrahydrofurane and sodium hydride, suspended in dioxane to yield the (3-tetrahydrofuryl)-benzylether which is an active herbicide against grassy weeds (German Offenlegungsschrift No. 2724675).

The compounds prepared according to the invention by monohalogenation of alkylbenzenes in the α-position are obtained in high yields, in general of more than 90%, and usually of more than 94% of the theoretical yields, relative to the alkylbenzene converted, and in particularly high purity, so that they can be employed for many applications without further purification.

As a result of the recycling, according to the invention of the uncoverted alkylbenzene (I), which is separated off from the reaction mixture after leaving the reaction space, high conversions, in general 80% or more of the alkylbenzene employed, can be achieved without interrupting the process.

It is suprising that in the process according to the invention a uniformly high selectivity is maintained even with high conversions, since in the batchwise process according to the prior art (Houben-Weyl, loc. cit., page 736), for example in the case of the chlorination of toluene, the process has to be discontinued at a 30% conversion in order to obtain a pure benzyl chloride.

It is also surprising that strict exclusion of moisture, as is required according to the prior art (Houben-Weyl, loc. cit., page 736), is not necessary in the process according to the invention.

BRIEF DESCRIPTION OF DRAWING

Referring to the accompanying drawing, the same in a side elevation of an apparatus particularly suited for carrying out the invention.

EXAMPLES

(A) Reaction apparatus

Figure 1:
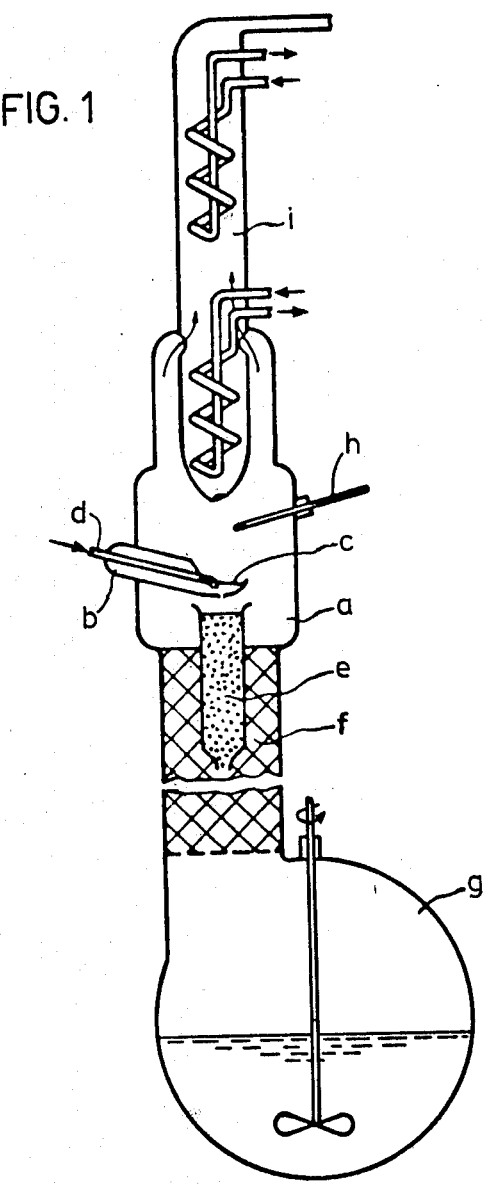

The reaction apparatus shown in the accompanying drawing is used in the examples which follow. The apparatus consists of a vaporizing vessel (g), which contains the starting compound. A column (f) which is filled with packing and into which an empty tube (e), which narrows towards the bottom, is inserted, is fitted on top of the vaporizing vessel (g). The reaction space (a), into which a device (b) is inserted, in which that portion located in the reaction space is designed as a recess (c), is located above the column (f). The halogen is fed from outside, through the inlet (d), into the device (b) to the recess (c) and, at the same time, the reaction space is irradiated with UV light. The thermometer (h) is also inserted in the reaction space (a) to check the reaction temperature. The condenser (i) is so arranged above the reaction space that the liquid component which condenses here can drip into the recess (c).

(B) Reactions

The reaction is illustrated by the following examples:

EXAMPLE 1

318 g of m-xylene are chlorinated in the apparatus described under (A). The heat supply to the vaporising vessel is so controlled that the amount of liquid xylene refluxing from the condenser (i) into the recess (c) is about 900 g/hour (about 8.5 mol/hour). After the reflux of m-xylene from the condenser has started, chlorine vapour is fed in an amount of 33 to 33.5 g/hour (about 0.47 mol/hour) through the inlet (d) to the recess (c). The reaction mixture flows through the hole in the recess (c) into the tube (e). It contains about 5 mol % of 3-methylbenzyl chloride. The chlorination is discontinued when the conversion is 86%. According to analysis by gas chromatography, the product mixture in the vaporizing flask contains 341 g of 3-methyl-benzyl chloride, which corresponds to a yield of 94%, based on converted m-xylene. After fractional distillation pure 3-methylbenzyl chloride is obtained; boiling point$_{13}$=84° C.; $n_D^{20}$=1.5354; purity according to analysis by gas chromatography 98.14%.

When the reaction is carried out continuously, chlorine and m-xylene are fed into the apparatus at the top while, at the same time, radiation with UV light is carried out continuously—and the chlorination product is continuously removed from the evaporator. The hydrochloric acid formed escapes at the top of the apparatus.

The examples listed in the table were carried out analogously to the above example.

| Example | Alkylbenzene | Degree of conversion | Product according to formula (I) and yield |
|---|---|---|---|
| 2 | toluene | 98.3% | 94% — C$_6$H$_5$—CH$_2$—Cl |
| 3 | o-xylene | 89% | 93% — o-CH$_3$-C$_6$H$_4$-CH$_2$Cl |
| 4 | p-xylene | 91% | 94% — p-CH$_3$-C$_6$H$_4$-CH$_2$Cl |
| 5 | mesitylene | 81% | 90.5% — 3,5-(CH$_3$)$_2$-C$_6$H$_3$-CH$_2$—Cl |
| 6 | o-CF$_3$-C$_6$H$_4$-CH$_3$ | 96% | 98% — o-CF$_3$-C$_6$H$_4$-CH$_2$—Cl |
| 7 | m-Cl-C$_6$H$_4$-CH$_3$ | 77% | 98.6% — m-Cl-C$_6$H$_4$-CH$_2$Cl |
| 8 | 2-CH$_3$-4-F-C$_6$H$_3$-NCO | 76.3% | 97% — 2-CH$_2$Cl-4-F-C$_6$H$_3$-NCO |
| 9 | C$_6$H$_5$-O-C$_6$H$_4$-CH$_3$ | 80% | 90% — C$_6$H$_5$-O-C$_6$H$_4$-CH$_2$Cl |
| 10 | o-Cl-C$_6$H$_4$-CH$_3$ | 96% | 99% — o-Cl-C$_6$H$_4$-CH$_2$Cl |

| Example | Alkylbenzene | Degree of conversion | Product according to formula (I) and yield |
|---|---|---|---|
| 11 | 2-chloro-toluene (Cl, CH3 on benzene) | 86% | 99% — 2-chloro-benzyl chloride (Cl, CH2—Cl on benzene) |
| 12a | 4-fluorophenyl ether of 3-methylphenol (F-C6H4-O-C6H4-CH3) | 34% | 90.3% — corresponding CH2Cl derivative |
| 12b | 4-methylbenzoyl chloride (H3C-C6H4-COCl) | 87% | 96.5% — Cl-CH2-C6H4-COCl |

The following compounds are obtained with an equally good result by the process of Example 1:

| 13 | 3-chloro-4-trifluoromethyl-benzyl chloride (Cl, CF3, CH2Cl on benzene) | Boiling point$_{12}$ 102° C. | $n_D^{20}$ 1.4936 |
| 14 | 2-(chloromethyl)phenyl chloroformate (CH2Cl, OCO—Cl on benzene) | Boiling point$_{12}$ 123° C. | $n_D^{20}$ 1.5379 |
| 15 | 4-(trifluoromethylthio)benzyl chloride (CF3S, CH2Cl) | Boiling point$_{15}$ 100° C. | $n_D^{20}$ 1.5070 |
| 16 | 4-(trifluoromethoxy)benzyl chloride (CF3O, CH2Cl) | Boiling point 185° C. | $n_D^{20}$ 1.4549 |
| 17 | 3-chloro-4-(trifluoromethoxy)benzyl chloride (CF3O, Cl, CH2Cl) | Boiling point$_{15}$ 100° C. | $n_D^{20}$ 1.4788 |
| 18 | 4-(bis-trifluoromethyl-fluoromethyl)benzyl chloride (F3C-FC(CF3)-C6H4-CH2Cl) | Boiling point$_{50}$ 109° C. | $n_D^{20}$ 1.4251 |
| 19 | 3,5-bis(trifluoromethyl)benzyl chloride (CF3, F3C, CH2Cl) | Boiling point$_{16}$ 68° C. | Melting point about 28° C. |
| 20 | 4-isocyanatobenzyl chloride (OCN, CH2Cl) | Boiling point$_{10}$ 117° C. | Melting point 34° C. |

EXAMPLES 21–24 (Comparison Examples)

For the alkylbenzenes listed in the table, a chlorination was carried out according to Example 1 with conversions of above 80% and the by-products obtained were determined. For comparison, a bottom phase chlorination according to the instructions in Houben-Weyl, Methoden der Organischen Chemie (Methods of Organic Chemistry), volume V/3, page 736, Verlag Georg Thieme, Stuttgart, 1962 was carried out and the degree of conversion at which the same amount of by-products is obtained was determined.

| | | Degree of conversion (%) | | |
|---|---|---|---|---|
| No. | Alkylbenzene | according to the invention | prior art | By-products (% by weight) |
| 21 | mesitylene | 81 | 40 | 7.6 |
| 22 | o-xylene | 88.5 | 43 | 5 |
| 23 | m-xylene | 86 | 40 | 5 |
| 24 | p-xylene | 85 | 43 | 5 |

What is claimed is:

1. A process for the selective monohalogenation of an alkylbenzene in the alpha-position comprising continuously contacting a stoichiometric excess of an alkylbenzene having at least one hydrogen atom in the alpha-position with a halogen at a temperature in the range of about 80° C. up to the boiling point of the alkylbenzene while applying UV radiation thereto while continuously withdrawing reaction mixture containing no more than about 33 mol percent of halogenoalkylbenzene product, based upon the number of mols of all of the substances contained in the reaction mixture, said alkylbenzene being vaporized from a collection vessel, the vapors being caused to flow upwardly through a defined reaction zone into a condensation zone, the so-vaporized alkylbenzene being condensed and liquid alkylbenzene being caused to flow downwardly into said defined reaction zone and toward said collection zone, the passage of said liquid alkylbenzene downwardly through said reaction zone being retarded, halogen gas being directed against the retarded liquid alkylbenzene and the thus formed halogenated alkylbenzene being passed into said collection vessel by directing condensed alkylbenzene thereagainst.

2. A process according to claim 1, wherein the halogen is chlorine.

3. A process according to claim 1, wherein the condensed alkylbenzene is retarded by collecting the same in a concave depression.

4. A process according to claim 1, wherein the alkylbenzene to be monohalogenated is in admixture with water in an amount up to its saturation concentration.

5. A process according to claim 1, wherein excess unreacted alkylbenzene in the reaction mixture is separated from the reaction mixture and recycled to the reaction zone.

6. A process according to claim 1, wherein alkylbenzene is an alkylbenzene of the formula

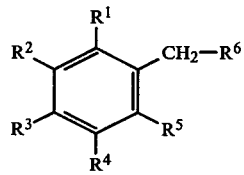

in which $R^1$ to $R^5$ can be identical or different and represent hydrogen, alkyl, halogenoalkyl, aryl, aralkyl, alkoxy, aryloxy, halogen, isocyanate, nitro, chlorosulphonyl, chlorocarbonyl or cyano and, in addition, two adjacent radicals $R^1$ to $R^5$ together can form an alkylene group, or together with the carbon atoms which carry them can represent a fused aromatic ring, and $R^6$ denotes hydrogen, halogen, alkyl or aryl.

7. A process according to claim 6, wherein when any of $R^1$ to $R^5$ represent alkyl they represent an alkyl radical having 1 to 4 carbon atoms, whenever any radicals $R^1$ to $R^6$ represent an aryl radical they represent a $C_6$ to $C_{14}$ aryl radical; when $R^1$ to $R^5$ represent a halogenoalkyl radical they represent a halogenoalkyl having 1 to 4 carbon atoms in the alkyl portion; when any of the radicals $R^1$ to $R^5$ represent an aralkyl radical they represent an aralkyl radical having 1 to 2 carbon atoms in the aliphatic portion and 6 to 14 carbon atoms in the aromatic portion, when any of the radicals $R^1$ to $R^5$ represent an alkoxy radical they represent a $C_1$ to $C_4$ alkoxy radical; when any of the radicals $R^1$ to $R^5$ represent an aryloxy radical they represent an aryloxy radical having 6 to 18 carboxylic carbon atoms; when any of the radicals $R^1$ to $R^5$ form an alkylene group they form an alkylene group having 3 to 4 carbon atoms and when any of the radicals $R^1$ to $R^5$ together with the carbon atoms they represent represent a fused aromatic ring they represent a ring of the naphthalene system.

8. A process according to claim 1, wherein the reaction mixture contains 2 to 50 mols of alkylbenzene per mol of halogen.

9. A process according to claim 1, wherein the reaction mixture contains 3 to 20 mols of alkylbenzene per mol of halogen.

10. A process according to claim 1, wherein the reaction is performed from a temperature of 30 degrees C. below the boiling point of the alkylbenzene up to the boiling point of the alkylbenzene.

11. A process according to claim 10, wherein the reaction is performed at a temperature from 10° C. below the boiling point of the alkylbenzene up to the boiling point thereof.

* * * * *

UNITED STATES PATENT AND TRADEMARK OFFICE
CERTIFICATE OF CORRECTION

PATENT NO. : 4,331,821
DATED : May 25, 1982
INVENTOR(S) : Rudiger Schubart etal

It is certified that error appears in the above—identified patent and that said Letters Patent is hereby corrected as shown below:

Title Page Insert --Feb. 10, 1979 [DE]
Priority     Fed. Rep. of Germany 2905081--.

Signed and Sealed this

Fifth Day of October 1982

[SEAL]

Attest:

GERALD J. MOSSINGHOFF

Attesting Officer       Commissioner of Patents and Trademarks